(12) United States Patent
Kofoed et al.

(10) Patent No.: US 9,681,958 B2
(45) Date of Patent: *Jun. 20, 2017

(54) ANKLE-JOINT ENDOPROSTHESIS

(71) Applicant: Stryker European Holdings I, LLC, Kalamazoo, MI (US)

(72) Inventors: Hakon Kofoed, Charlottenlund (DK); Arnold Keller, Kayhude (DE); Helmut D. Link, Hamburg (DE)

(73) Assignee: Stryker European Holdings I, LLC, Kalamazoo, MI (US)

( * ) Notice: Subject to any disclaimer, the term of this patent is extended or adjusted under 35 U.S.C. 154(b) by 211 days.

This patent is subject to a terminal disclaimer.

(21) Appl. No.: 14/088,524

(22) Filed: Nov. 25, 2013

(65) Prior Publication Data

US 2014/0081413 A1    Mar. 20, 2014

Related U.S. Application Data

(63) Continuation of application No. 12/755,086, filed on Apr. 6, 2010, now Pat. No. 8,591,595, which is a
(Continued)

(51) Int. Cl.
*A61F 2/42* (2006.01)
*A61F 2/30* (2006.01)

(52) U.S. Cl.
CPC ........ *A61F 2/4202* (2013.01); *A61F 2/30734* (2013.01); *A61F 2002/3028* (2013.01);
(Continued)

(58) Field of Classification Search
CPC .... A61F 2/4202; A61F 2/4205; A61F 2/4207; A61F 2/421; A61F 2/4212; A61F 2/4215;
(Continued)

(56) References Cited

U.S. PATENT DOCUMENTS 4,069,518 A    1/1978  Groth, Jr. et al.
4,470,158 A    9/1984  Pappas et al.
(Continued)

FOREIGN PATENT DOCUMENTS

DE    8812806 U1    11/1988
DE    3904004 A1     8/1990
(Continued)

OTHER PUBLICATIONS

International Search Report dated Jun. 3, 2004 for PCT/EP03/09489.
(Continued)

*Primary Examiner* — David H Willse
(74) *Attorney, Agent, or Firm* — Lerner, David, Littenberg, Krumholz & Mentlik, LLP

(57) ABSTRACT

An endoprosthesis for replacing the ankle joint includes a lower component which is configured to be connected to the ankle bone, an upper component which is configured to be connected to the shin bone, and an intermediate part which forms a slide joint both with the lower and upper components. The intermediate part, which is wedge-shaped in sagittal section, is provided in order to compensate for anatomical or surgical irregularities. The upper component can also be wedge-shaped in frontal or sagittal section.

12 Claims, 1 Drawing Sheet

Related U.S. Application Data continuation of application No. 10/567,580, filed as application No. PCT/EP03/09489 on Aug. 27, 2003, now abandoned.

(52) U.S. Cl.
CPC ............. *A61F 2002/3082* (2013.01); *A61F 2002/30153* (2013.01); *A61F 2002/30158* (2013.01); *A61F 2002/30233* (2013.01); *A61F 2002/30266* (2013.01); *A61F 2002/30281* (2013.01); *A61F 2002/30324* (2013.01); *A61F 2002/30382* (2013.01); *A61F 2002/30395* (2013.01); *A61F 2002/30398* (2013.01); *A61F 2002/30433* (2013.01); *A61F 2002/30604* (2013.01); *A61F 2002/30616* (2013.01); *A61F 2002/30621* (2013.01); *A61F 2002/30736* (2013.01); *A61F 2002/30878* (2013.01); *A61F 2002/30881* (2013.01); *A61F 2002/30892* (2013.01); *A61F 2002/30934* (2013.01); *A61F 2220/0025* (2013.01); *A61F 2220/0033* (2013.01); *A61F 2220/0041* (2013.01); *A61F 2230/0019* (2013.01); *A61F 2230/0026* (2013.01); *A61F 2230/0063* (2013.01); *A61F 2230/0069* (2013.01); *A61F 2230/0082* (2013.01); *A61F 2250/0036* (2013.01); *A61F 2310/00011* (2013.01); *A61F 2310/00179* (2013.01)

(58) Field of Classification Search
CPC .............. A61F 2/4217; A61F 2/422; A61F 2002/4205; A61F 2002/4207; A61F 2002/421; A61F 2002/4212; A61F 2002/4215; A61F 2002/4217; A61F 2002/422
USPC ...................................... 623/21.18
See application file for complete search history.

(56) References Cited

U.S. PATENT DOCUMENTS

| | | | |
|---|---|---|---|
| 4,904,269 A | 2/1990 | Elloy et al. | |
| 5,019,103 A | 5/1991 | Van Zile et al. | |
| 5,133,758 A | 7/1992 | Hollister | |
| 5,152,797 A | 10/1992 | Luckman et al. | |
| 5,458,637 A | 10/1995 | Hayes | |
| 5,728,161 A | 3/1998 | Camino et al. | |
| 5,824,106 A | 10/1998 | Fournol | |
| 6,008,433 A | 12/1999 | Stone | |
| 6,053,945 A | 4/2000 | O'Neil et al. | |
| 6,183,519 B1 | 2/2001 | Bonnin et al. | |
| 6,409,767 B1 | 6/2002 | Perice et al. | |
| 6,540,786 B2 | 4/2003 | Chibrac et al. | |
| 6,673,116 B2 | 1/2004 | Reiley | |
| 6,852,130 B2 | 2/2005 | Keller et al. | |
| 6,863,691 B2 | 3/2005 | Short et al. | |
| 6,926,739 B1 | 8/2005 | O'Connor et al. | |
| 6,939,380 B2 | 9/2005 | Guzman | |
| 7,011,687 B2 | 3/2006 | Deffenbaugh et al. | |
| 7,025,790 B2 | 4/2006 | Parks et al. | |
| 7,625,409 B2 | 12/2009 | Saltzman et al. | |
| 2003/0181985 A1 | 9/2003 | Keller et al. | |
| 2004/0030399 A1 | 2/2004 | Asencio | |
| 2006/0235421 A1 | 10/2006 | Rosa et al. | |
| 2010/0198355 A1 | 8/2010 | Kofoed et al. | |
| 2010/0212138 A1 | 8/2010 | Carroll et al. | |
| 2012/0130434 A1 | 5/2012 | Stemniski | |
| 2012/0271314 A1 | 10/2012 | Stemniski et al. | |

FOREIGN PATENT DOCUMENTS

| | | |
|---|---|---|
| DE | 20010346 U1 | 8/2000 |
| DE | 10123124 C1 | 12/2002 |
| EP | 1097680 A1 | 5/2001 |
| FR | 2676917 A1 | 12/1992 |
| WO | 00/69373 A1 | 11/2000 |
| WO | 0189427 A1 | 11/2001 |
| WO | 03075802 A1 | 9/2003 |

OTHER PUBLICATIONS

Machine generated translation of DE 39 04 004 A1 (Aug. 16, 1990).
Machine generated translation of DE 101 23 124 C1 (Dec. 19, 2002).
Kofoed, Hakon et al., U.S Office Action mailed on Oct. 23, 2007 directed at U.S. Appl. No. 10/567,580; 9 pages.
Kofoed, Hakon et al., U.S Office Action mailed on Sep. 15, 2008 directed at U.S. Appl. No. 10/567,580; 6 pages.
Kofoed, Hakon et al., U.S Office Action mailed on Feb. 27, 2009 directed at U.S. Appl. No. 10/567,580; 6 pages.
Kofoed, Hakon et al., U.S Office Action mailed on Oct. 6, 2009 directed at U.S. Appl. No. 10/567,580; 5 pages.
Small Bones Innovations, Inc., Star™ Surgical Technique, 2009-2013.

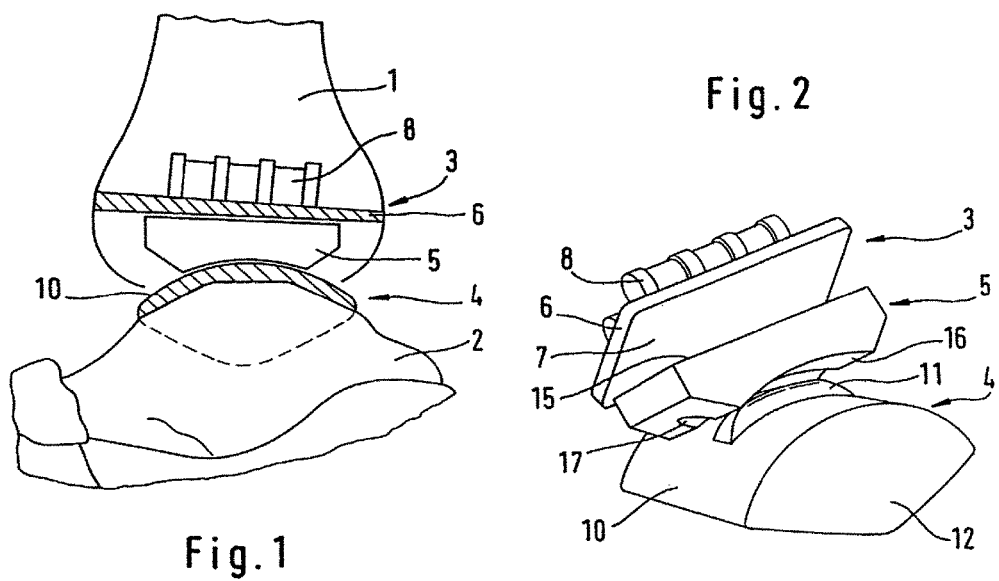
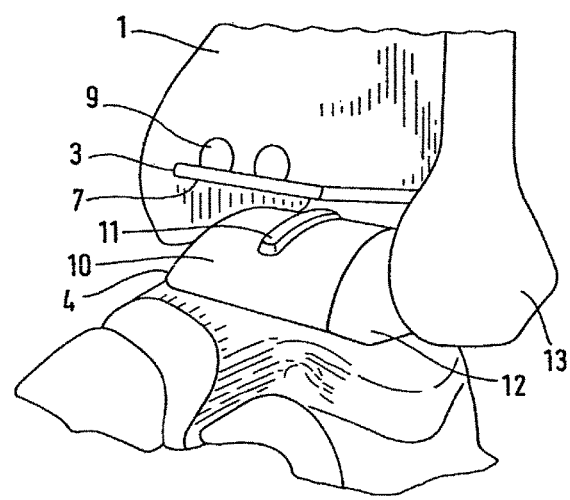
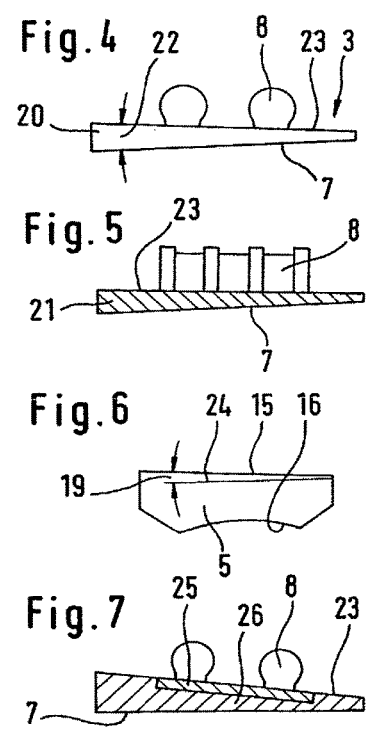

ANKLE-JOINT ENDOPROSTHESIS

CROSS REFERENCE OF RELATED APPLICATIONS

This application is a continuation of U.S. application Ser. No. 12/755,086, filed Apr. 6, 2010, now U.S. Pat. No. 8,591,595, which is a continuation of U.S. application Ser. No. 10/567,580, filed Feb. 8, 2006, which is a National Stage application of PCT/EP2003/009489, filed Aug. 27, 2003, the contents of which are incorporated herein by reference in their entireties.

FIELD AND BACKGROUND OF THE INVENTION

To replace the ankle joint, an endoprosthesis is known comprising a component to be connected to the ankle bone, a component to be connected to the shin bone, and an intermediate part (DE-U-88 12 806, brochure "LINK S.T.A.R. Totale Sprunggelenk-prothese [H. Kofoed] from Waldemar Link (GmbH & Co.), Hamburg). The ankle bone component and the intermediate part interact via slide surfaces which permit flexion and extension in the sagittal plane. The shin bone component and the intermediate part form interacting slide surfaces which permit a rotation about the vertical axis of the endoprosthesis. They can be of a plane design in order to permit compensating movements in the antero-posterior (AP) direction and latero-medial (LM) direction. Stabilization is afforded by the natural ligament apparatus.

In the known prosthesis, the top and bottom slide surfaces of the intermediate part are oriented parallel to one another in the frontal plane because the prosthetic replacement of the joint is not intended to result in a change in direction. However, it has been found that, after surgery, the collateral and medial ligaments of the joint often have different tensioning, which can cause problems. This may be due to irregularities of the anatomy or to the fact that the operating surgeon has chosen an unfavorable orientation of the resection surface provided on the shin bone for connection to the prosthesis.

SUMMARY OF THE INVENTION

The object of the invention is to avoid or alleviate an imbalance between, on the one hand, the anatomical or surgical circumstances and, on the other hand, the prosthesis.

The solution according to the invention lies in the features of the invention as disclosed more broadly and more specifically below. Accordingly, the intermediate part and/or the shin bone component are of a wedge-shaped design. If the operating surgeon finds that the ligament tension is different if a normal prosthesis is used, he can compensate for this by using corrective components which have a wedge shape in the frontal plane. The thicker side of the wedge-shaped corrective plate is arranged on that side on which the ligament tension would be inadequate if normal components were used. If he finds that the tibial resection surface is not perpendicular to the tibial direction or if he wishes, for other reasons, that the prosthesis planes do not extend perpendicular with respect to the axis of the tibia, he can also use corrective components whose wedge shape lies in the sagittal plane. If the operating surgeon wishes that the lower slide surface of the upper component has a defined orientation with respect to the tibial direction or the direction of loading, he will generally use a shin bone component designed as corrective component. If, by contrast, the orientation of the tibial resection surface is correct and the aim is to take account of the anatomy of the foot, he will prefer an intermediate part designed as corrective component.

This application does not relate to the wedge-shaped design of the intermediate part in the frontal plane since this is the subject matter of the earlier, not prior published patent application PCT/EP02/02573, published in the United States as U.S. Patent Publication No. 2003-0181985-A1, and now U.S. Pat. No. 6,852,130.

Determining that the upper component is wedge-shaped does not in practice cause any difficulties since both its top connection surface and also its bottom slide surface are planar or substantially planar. Comparison with the normal intermediate parts is decisive in determining any wedge shape of the intermediate part in the sagittal plane. Moreover, it is not only simple to determine the direction of the approximately planar top slide surface of the intermediate part, but also the overall orientation of the bottom slide surface. An intermediate part is wedge-shaped, within the meaning of the present invention, in the sagittal plane when it becomes thicker anteriorly or posteriorly compared to the normal intermediate part.

A wedge shape in the sagittal plane can, in the context of the present invention, be combined with a wedge shape in the frontal plane. However, the wedge shape can occur in the sagittal or frontal plane also without a wedge shape in the frontal or sagittal plane.

The wedge angle is expediently between 1° and 16°, preferably between 3° and 8°.

To ensure that the orientation of the wedge shape of the intermediate part cannot be altered by rotation of the intermediate part about the vertical axis, its orientation is expediently forcibly fixed by way of the ankle bone or the shin bone, by means of the interacting slide surface pairs being designed accordingly in a manner which defines a direction (for example cylindrically). The joint between the ankle bone and the intermediate part is particularly suitable for this purpose.

To ensure that the operating surgeon can choose between different wedge angles, he must have access to several different corrective components for each prosthesis. To reduce the costs associated with this, it is expedient to design the corrective components as simply as possible. It may therefore be expedient for them to be made up of an unchanging standard part and of a wedge part. The standard part is provided in only one configuration. Only the wedge parts need to be provided in different variants. This applies in particular if the upper component is used as corrective component and the standard part forms the means necessary for securing to the shin bone.

BRIEF DESCRIPTION OF THE DRAWINGS

The invention is explained in greater detail below with reference to the drawing which depicts advantageous illustrative embodiments and in which:

FIG. 1 shows a sagittal section through a joint fitted with the prosthesis,

FIG. 2 shows the prosthesis in a perspective view and opened out,

FIG. 3 shows a perspective view of the arrangement of the implanted upper and lower prosthesis components before the intermediate part is inserted, FIG. 4 shows a frontal section through an upper corrective component, FIG. 5 shows a sagittal section through an upper corrective component, FIG. 6 shows a sagittal section through a corrective intermediate part, and FIG. 7 shows an upper corrective component which is designed in two parts.

DETAILED DESCRIPTION OF THE INVENTION

The prosthesis comprising the upper component 3, the lower component 4 and the intermediate part 5 is to be arranged between the shin bone 1 and the ankle bone 2. The upper component 3 has a plate-shaped part 6 whose bottom face 7 forms a planar slide surface. Projections 8 are used for securing it in corresponding resection recesses 9 in the shin bone 1.

The lower component 4 forms a convexly curved slide surface 10 which can be designed cylindrically or conically. It carries a rib 11 which lies in the direction of the relative movement of the intermediate part during flexion and extension movement. The lower component additionally has lateral facets 12 for interaction with corresponding slide surfaces of the shin bone 1 and of the calf bone 13.

The intermediate part 5 has a planar top face 15 matching the slide surface 7, and a bottom slide surface 16 which is designed to complement the slide surface 10 of the lower component 4. It includes a groove 17 for receiving the rib 11. In this way, the intermediate part 5 is guided laterally in relation to the lower component 4. It is allowed only flexion and extension movements.

The upper and lower components 3 and 4 are expediently made of metal, and the intermediate part 5 of a plastic that promotes sliding, for example polyethylene. However, other materials with sufficient strength and slidability can also be used, for example ceramic.

On account of the complementary shape of the slide surfaces 10 and 16, and by the rib 11 interacting with the groove 17, the intermediate part 5 is nonrotatable about the vertical axis in relation to the ankle joint component 4. Its orientation is thus fixed by that of the lower component. While the embodiment shown completely rules out rotation movements of this kind between the lower component and the intermediate part about the vertical axis, configurations are also conceivable in which these are permitted within predetermined limits or are merely inhibited by the design of the slide surfaces or are not ruled out.

The above explanation with reference to FIGS. 1 through 3 applies both to designs with normal components and also to designs with corrective components.

FIGS. 4 through 6 show examples of corrective components. FIG. 4 shows a frontal view of an upper component 3 designed as corrective component. Near the edge 20 appearing on the left in the drawing, it is thicker than at the opposite edge. The component is designed symmetrically in relation to its frontal midplane, such that the thickened side 20 may lie on the lateral side or medial side of the joint, depending on the choice made by the operating surgeon.

FIG. 5 shows a sagittal section through the upper component 3. It is thickened in a wedge shape at the end 21 appearing on the left in the drawing. The top face of this component is symmetrical in relation to the frontal plane. Therefore, the thickened end can be arranged anteriorly or posteriorly in the joint, depending on the choice made by the operating surgeon. The wedge angle 22 between the top securing surface 23 and the lower slide surface 7 is of the order of magnitude of 5° in both examples.

FIG. 6 shows a sagittal section through a corrective intermediate part 5. Its bottom face 16 designed as slide surface has an overall orientation extending approximately parallel to the auxiliary line 24 which has been drawn in order to illustrate the wedge angle 19 near the top slide surface 15. In this case it is assumed that the line 24 in the normal intermediate parts extends parallel to the overall direction of the bottom face 16. The critical factor in determining a wedge shape of the intermediate part is always the comparison with the normal components of the prosthetic system.

It is not necessary for a correction to be restricted in each case to just one component. Instead, corrective components can be used both for the upper component and also for the intermediate part. This possibility is shown in FIG. 1.

As soon as the operating surgeon has implanted the lower component 4, he can use suitable instruments to determine whether, when the collateral ligaments are tensioned, the resection surface 25 of the shin bone has a normal extension relative to the lower component 4 or whether a correction is necessary. In the latter case, he decides whether a corrective component needs to be selected for the upper component or the intermediate part or for both and he decides how pronounced the respective wedge shape needs to be and in what direction it should lie. A corresponding measurement is also still possible when the upper component 3 has been fitted. Thereafter, it is possible to decide whether a corrective component is to be used as intermediate part.

FIG. 7 illustrates the composition of the upper component 3 made up of a standard part 25 and a wedge part 26. Since the standard part 25 forms the securing members 8, the wedge part 26, of which several examples with varying wedge angles are made available, can be made correspondingly simpler. The two parts can be connected to one another in any desired and known manner. For example, they can be screwed together. They can also be provided with complementary projections and recesses engaging in one another, making it possible to join the two parts together without any great effort.

The invention claimed is:

1. An endoprosthesis for replacing an ankle joint, comprising:
    a lower component which is configured to be connected to an ankle bone and which forms a top slide surface,
    a plate shaped upper component which forms a planar or substantially planar bottom slide surface and which has a top connection surface including at least one projection extending from the plate shape, the top connection surface configured for connection to a resection surface of a shin bone, and
    an intermediate part which has two slide surfaces interacting with the top and bottom slide surfaces of the upper and lower components, the slide surface of the intermediate part interacting with the bottom slide surface of the upper component being planar or substantially planar,
    wherein the upper component forms a first wedge angle greater than 1° in a frontal or sagittal section of the plate shape or the intermediate part forms a second wedge angle greater than 1° in a sagittal section between its top slide surface and an auxiliary line extending parallel to an overall orientation of its bottom slide surface, wherein either the first or second wedge angle extends in a consistent direction along the upper component or intermediate part respectively.

2. The endoprosthesis as claimed in claim 1, wherein the interacting slide surfaces on the lower component and the intermediate part interact substantially nonrotatably with respect to a vertical axis of the endoprosthesis.

3. The endoprosthesis as claimed in claim 1, wherein the interacting slide surfaces on the upper component and the intermediate part interact rotatably with respect to a vertical axis of the endoprosthesis.

4. The endoprosthesis as claimed in claim 1, wherein the angles associated with the upper component and the intermediate part are between 1° and 16°.

5. The endoprosthesis as claimed in claim 1, wherein the angles associated with the upper component and the intermediate part are between 3° and 8°.

6. A system of endoprosthesis for replacing the ankle joint, comprising a plurality of sets of endoprosthesis, each set comprising:
   a lower component which is configured to be connected to an ankle bone and comprises a top slide surface,
   an upper component which comprises a planar or substantially planar bottom slide surface and a top connection surface configured for connection to a resection surface of a shin bone, and
   an intermediate part which comprises two slide surfaces configured for interacting with the top and bottom slide surfaces of the upper and lower components, the slide surface of the intermediate part configured for interacting with the bottom slide surface of the upper component being planar or substantially planar,
   the system comprising sets of first upper components whose top and bottom faces are substantially parallel and first intermediate parts whose top faces are substantially parallel with the overall direction of their bottom faces and sets of either corrective upper components which are configured for exchange for the first upper components and which are not substantially parallel in their sagittal or frontal planes between their top and bottom faces or corrective intermediate parts which are configured for exchange for the first intermediate parts and which, between their top faces and the overall direction of the bottom faces, are not substantially parallel in the sagittal plane as compared to the first intermediate parts.

7. The endoprosthesis as claimed in claim 6, wherein at least one of the corrective upper components comprises a separable wedge-shaped part having one of a varying number of wedge angles and a non wedge-shaped part having no wedge angle, wherein the wedge-shaped part includes the planar or substantially planar bottom slide surface of the upper component and the non wedge-shaped part includes the top connection surface of the upper component.

8. An endoprosthesis for replacing an ankle joint, comprising:
   a lower component which is configured to be connected to an ankle bone and which forms a top slide surface,
   an upper component having a separable wedge-shaped part having one of a varying number of wedge angles and a non wedge-shaped part having no wedge angle, wherein the wedge-shaped part includes a planar or substantially planar bottom slide surface of the upper component and the non wedge-shaped part includes a top connection surface of the upper component configured for connection to a resection surface of a shin bone, and
   an intermediate part which has two slide surfaces interacting with the top and bottom slide surfaces of the upper and lower components, the slide surface of the intermediate part interacting with the bottom slide surface of the upper component being planar or substantially planar,
   wherein the upper component forms a first wedge angle greater than 1° in a frontal or sagittal section between its bottom slide surface and its top connection surface or the intermediate part forms a second wedge angle greater than 1° in a sagittal section between its top slide surface and an auxiliary line extending parallel to an overall orientation of its bottom slide surface.

9. The endoprosthesis as claimed in claim 8, wherein the interacting slide surfaces on the lower component and the intermediate part interact substantially nonrotatably with respect to a vertical axis of the endoprosthesis.

10. The endoprosthesis as claimed in claim 8, wherein the interacting slide surfaces on the upper component and the intermediate part interact rotatably with respect to a vertical axis of the endoprosthesis.

11. The endoprosthesis as claimed in claim 8, wherein the angles associated with the upper component and the intermediate part are between 1° and 16°.

12. The endoprosthesis as claimed in claim 8, wherein the angles associated with the upper component and the intermediate part are between 3° and 8°.

* * * * *